United States Patent
Cinbis et al.

[11] Patent Number: 5,897,577
[45] Date of Patent: Apr. 27, 1999

[54] PACING LEAD IMPEDANCE MONITORING CIRCUIT AND METHOD

[75] Inventors: Can Cinbis, Shoreview; James D. Reinke, Maple Grove; Todd M. Tanji, Egan, all of Minn.

[73] Assignee: Medtronic, Inc., Minneapolis, Minn.

[21] Appl. No.: 08/965,801

[22] Filed: Nov. 7, 1997

[51] Int. Cl.⁶ .................................................. A61N 1/37
[52] U.S. Cl. ............................................................ 607/28
[58] Field of Search .................................. 607/28, 27, 30, 607/2, 4–9, 39–46, 52, 62, 63; 600/547, 506

[56] References Cited

U.S. PATENT DOCUMENTS

| | | | |
|---|---|---|---|
| 4,140,131 | 2/1979 | Dutcher et al. | 128/419 PT |
| 4,549,548 | 10/1985 | Wittkampf | 128/419 PG |
| 4,606,349 | 8/1986 | Livingston et al. | 128/419 PG |
| 4,899,750 | 2/1990 | Ekwall | 128/419 PG |
| 5,003,975 | 4/1991 | Hafelfinger et al. | 128/419 PG |
| 5,137,021 | 8/1992 | Wayne | 128/419 PT |
| 5,156,149 | 10/1992 | Hudrlik | 128/419 PG |
| 5,184,614 | 2/1993 | Collins et al. | 128/419 PG |
| 5,201,808 | 4/1993 | Steinhaus et al. | 128/419 PG |
| 5,201,865 | 4/1993 | Kuehn et al. | 128/419 PT |
| 5,350,410 | 9/1994 | Kleks et al. | 607/28 |
| 5,431,692 | 7/1995 | Hanson et al. | 607/28 |
| 5,534,018 | 7/1996 | Wahlstrand et al. | 607/27 |
| 5,741,311 | 4/1998 | Mc Venes et al. | 607/28 |
| 5,814,088 | 9/1998 | Paul et al. | 607/28 |

Primary Examiner—William E. Kamm
Assistant Examiner—Kennedy J. Schaetzle
Attorney, Agent, or Firm—Harold R. Patton; Michael B. Atlass

[57] ABSTRACT

A circuit for determining lead impedance during the time a pacing or other stimulating electrical pulse is being delivered measures current and voltage simultaneously to check for open circuits or short circuits based on different thresholds. The detection of a bad lead can force a double pulse to be delivered in real time in a unipolar configuration. Switching from unipolar to bipolar configuration based on detecting a bad bipolar circuit can be supported.

20 Claims, 7 Drawing Sheets

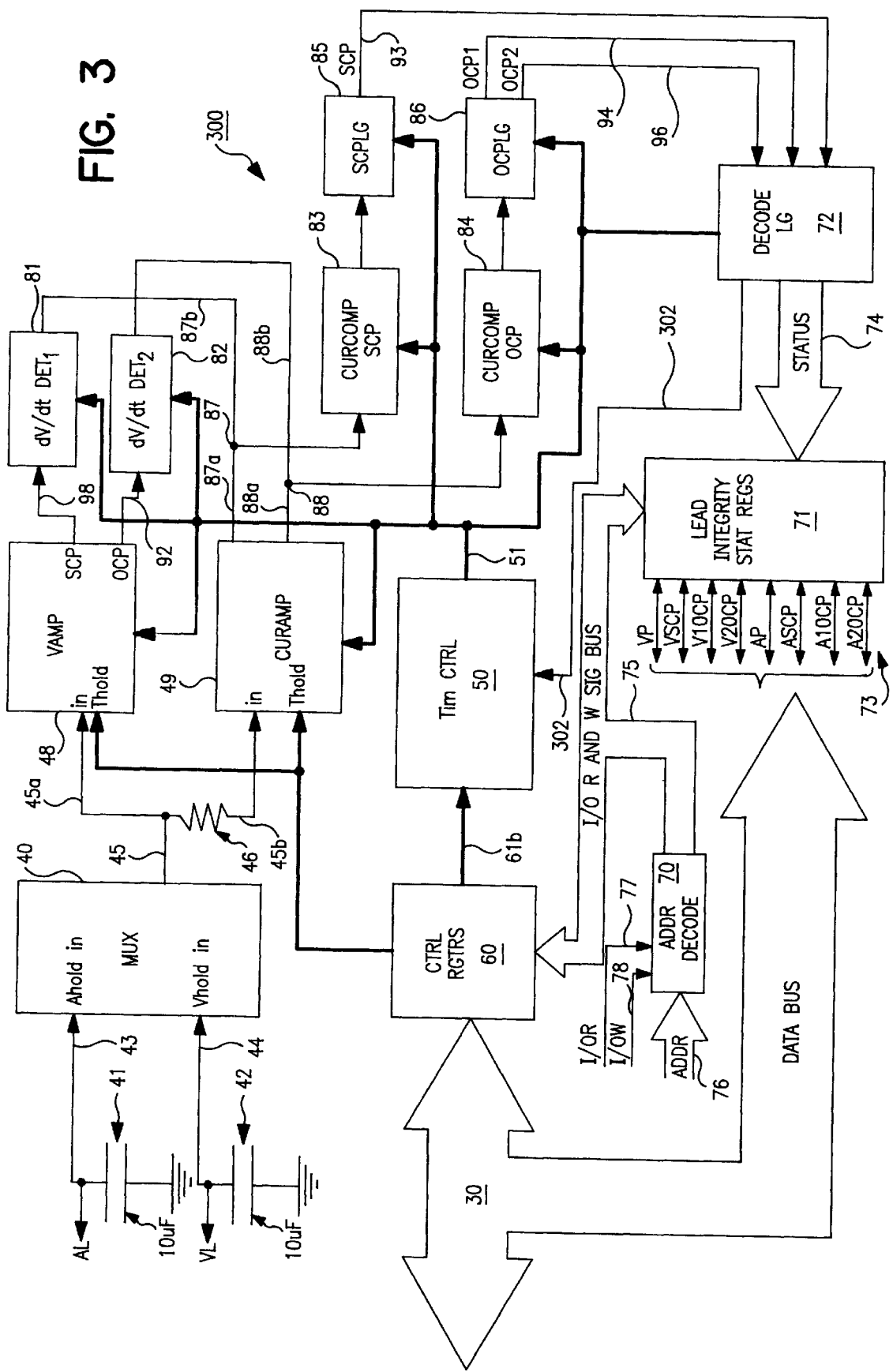

PACING LEAD IMPEDANCE MONITORING CIRCUIT AND METHOD

FIELD OF INVENTION

This invention relates to the field of implantable pulse generators and to the determination of lead impedance for such implantable medical devices.

BACKGROUND

Implantable pulse generators are now being used for cardiac pacemakers, defibrillator, cardioverters, neuro stimulators including those with leads implanted into the brain for controlling tremor, those with leads implanted into the spine for controlling continuous pain, and so forth. A problem common to all such devices includes the determination of the ability of the lead to transmit energy and a way to provide a reliable measurement of this lead capability.

In particular, implantable pulse generators used for pacing a patient's heart, pacemakers, may perform a critical function without which the patient may die nearly immediately, that is it may provide the stimulus required to keep the heart beating in cases of heart block and in cases where the patient has obtained a transplanted heart, for example.

If a lead essential to pacing the heart were to fail, automatic response to such failure may mean the difference between the life and the death of the patient. Accordingly, for many years since the start of cardiac pacing, the issue of the integrity of the conductors for conducting electrical stimulating pulses to pace the heart from the implanted pulse generator to the site of connection to the heart has been a serious concern and many solutions have been proposed to both provide for automatic responsiveness by shifting the pacing pulse from a bad conductor to an alternative good conductor and to creating at least a minimal historical record of the measurements of the pacing lead conductors impedance so as to generate data which can be used to redesign a next generation of leads or possibly to warn of an impending lead conductor failure.

The reason this problem is particularly acute in heart pacing is because lead conductors are usually metal which flexes constantly under the repeated motions of the heart causing metal fatigue, pacing leads are also susceptible to the possibility of insulation failure which would expose the metal conductors to the environment of the body which is particularly hostile to maintaining small metal wires or coils of wires in optimum condition.

In U.S. Pat. No. 5,003,975 issued to Hafelfinger et al, a good description of prior art solutions may be found. It describes U.S. Pat. Nos. 4,140,131 (Dutcher et al.), 4,549,548 (Wittkampf et al); 4,606,349 (Livingston et al.); and these patents are hereby incorporated by this reference hereto in their entireties. Additional patents by Walhstrand et al, U.S. Pat. Nos. 5,534,018; Kuehn, 5,201,865, Steinhaus et al, 5,201,808 Hudrlik, 5,156,149, Wayne et al, 5,137,021 Ekwall, 4,899,750; Collins, 5,184,614; and et al, 5,350,410; and Hansen et al, 5,431,692; also describe method and apparatus for sensing and using lead impedance for determining the integrity and or connection of lead conductors to the heart. Accordingly, these patents are also incorporated by this reference hereto in their entireties. Most of these patents listed above depend on the generation of an impedance reading during a period of time when the pacemaker is not providing a stimulation pulse to the heart or alternatively they sample and hold some portion or portions of a pacing signal, digitize some characteristic or characteristics inherent in that signal and have that digitized signal representation considered by a program run by a microprocessor in order to produce a signal value or a number indicating a good or bad value for the conductor under test.

What the art has not yet shown is a practical system through which the pacing pulse may be used to derive an impedance measurement based integrity value nearly contemporaneously with the pacing pulse and without requiring significant microprocessor involvement or power usage. Ideally such a system would be able to distinguish between short or open circuits in the pacing path (or other stimulator pathway) and enable the implantable pulse generator to switch to alternative pathways within a single cardiac cycle.

SUMMARY OF THE INVENTION

An object of this invention is to provide a teaching of circuitry within an implantable pulse generator which can determine the status of the stimulation pulse circuits contemporaneously with the provision of the stimulation pulse through such circuits.

A measurement of the derivative of the voltage combined with a measurement of the current proportional to the voltage taken from the stimulating pulse discharge mechanism produces a value that is compared to a predetermined threshold value adopted for the particular stimulating or pacing lead under test. If the combined voltage derivative and current signals are within the range indicted by the predetermined threshold for the particular pacing lead, the pacing lead impedance can be determined to be of an acceptable or unacceptable impedance for the condition (whether open or short) being tested with that stimulation pulse wave.

Different thresholds are used for open circuit testing and short circuit testing. In devices with multiple stimulation circuits under test, information relating to the timing of the stimulating pulse being delivered and measured, is used to decode which circuit is being tested as well as to determine the thresholds against which the measurements are made.

Additionally, use of a unipolar pace to facilitate capture at the time a bipolar pace problem is discovered and use of multiple means to test leads together with the one described herein are taught.

BRIEF DESCRIPTION OF THE DRAWINGS

FIG. 3 is a schematic block circuit diagram of the circuit elements and the connections therebetween housed within the IPG and providing for implantation of a preferred embodiment of the invention.

DETAILED DESCRIPTION OF PREFERRED EMBODIMENTS

Figure 1:
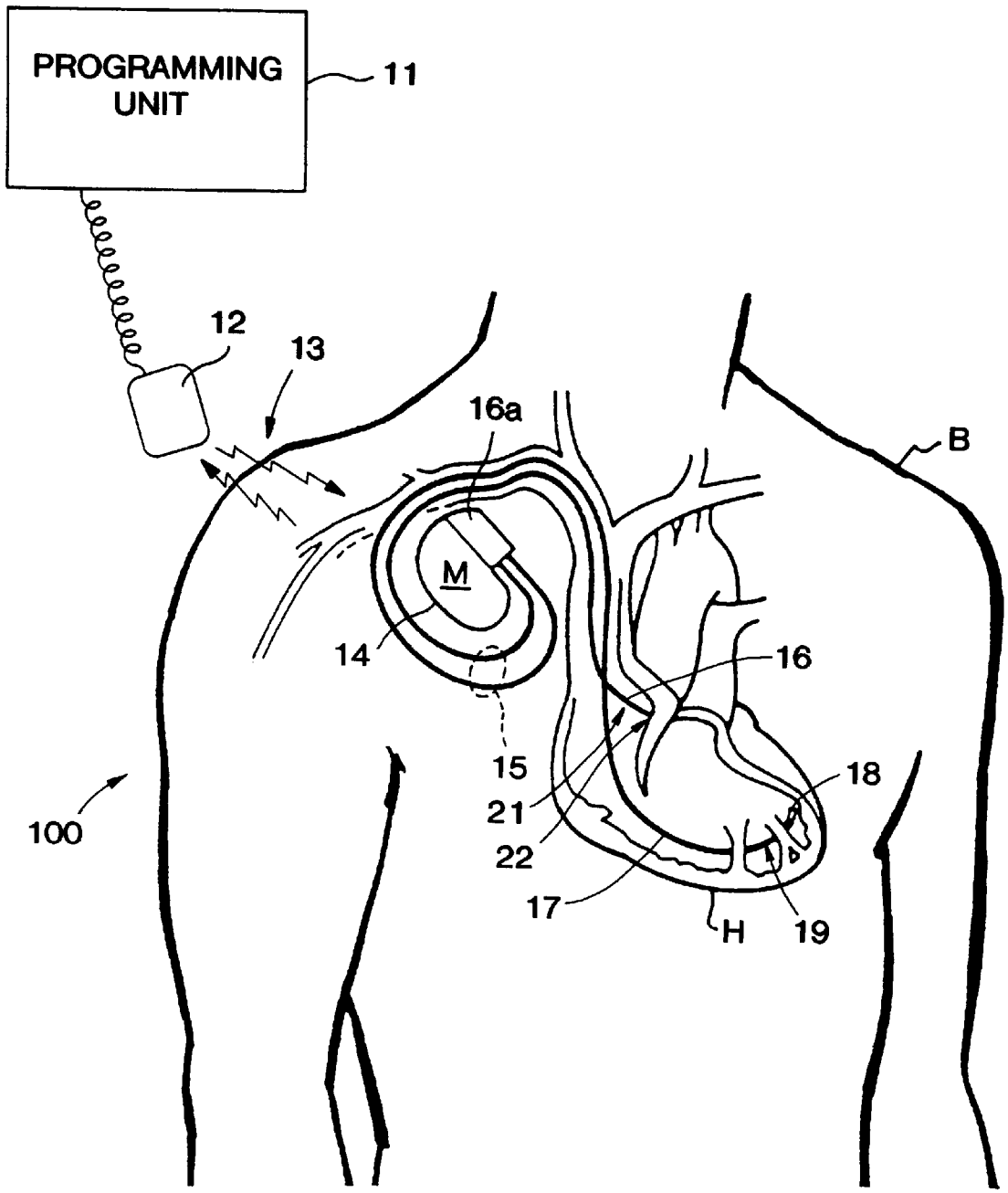
FIG. 1 is a heuristic diagram including an outline of a patient's body and his heart and the association therewith of an implantable pulse generator (IPG) used for preferred embodiments of this invention, as well as a communications device for communicating with said IPG.

Referring first to FIG. 1, an illustration of the system 100 associated with a patient's body B is shown. An implantable pulse generator (IPG) 14, in this embodiment a pacemaker, has a connector block 16a for providing electrical connection to both a ventricular lead 17 having a ring electrode located at 19 and a tip electrode located at point 18 with conductors therein providing for electrical connection from those points 18 and 19 through conductors in the Lead 17 to the IPG 14 at its housing M usually a hermetically sealed titanium "can." Additionally a lead 16 is shown implanted in the atrium of the heart H having a tip electrode at 22 and a ring electrode at 21 also with conductors providing electric pathways to said electrodes from said connector block 16a. The connector block is used to electrically isolate the conductors in the leads from the can or other surface electrodes that might be used with the IPG. In the housing M of the IPG 14 are located electrical circuits and components described later. The housing M is hermetically sealed and has electrical connectors which provide for electrical connections from the lead connectors in lead 15 through the connector block 16a and into the circuits within the hermetically sealed housing M. As is typically the case, IPG 14 can communicate through RF communication 13 with a programming unit 11, which typically employs a head 12 to hold close to the patient's body B so as to reduce the power requirements for transmission of telemetry from the IPG 14.

Figure 2:
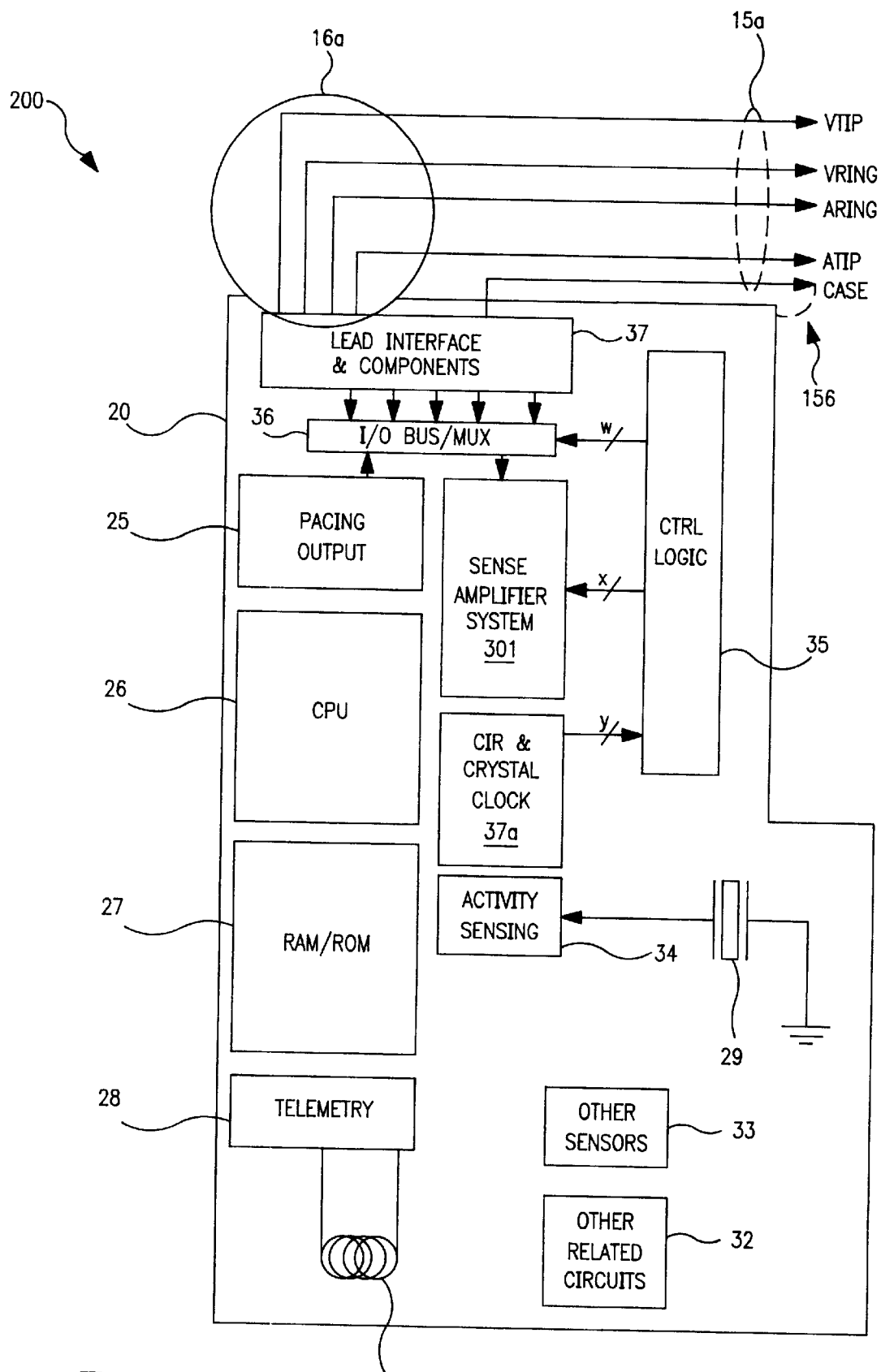
FIG. 2 is a heuristic block diagram representing the main components of a pacemaker system that may be used to implement a preferred embodiment of the invention.

Referring now to FIG. 2, the parts of the typical pacemaker type IPG 200 are illustrated in some detail. Four conductors 15a pass through the leads 15 in FIG. 1. These provide for electrical connections through the leads to the electrodes on the leads from the components in can 20.

Typically also, an electrode 15b is provided for connection to the case or housing of the hermetically sealed IPG. The conductors 15a pass through connector block 16a. A lead interface 37 is provided within the hermetically sealed housing so as to provide connection to both components and integrated circuits within the housing. These components may include the holding capacitors which are typically used in current generation IPG's to provide the current for the stimulating pulses delivered over the electrodes 15a as is well known in the art. Typically, the stimulating or stimulation circuit in bipolar pacing runs from Vtip or Atip in the ventricle or the atrium respectively to Vring and Aring electrodes through the heart tissue and or other body tissues and fluids. In unipolar pacing, the connection through the body tissue commonly goes from the tip electrode to the case electrode (15b). All variations in providing stimulating circuits are known, but these two just described arrangements are the most common.

Within the IPG 200 case 20 (usually built of titanium although ceramics and other metals and plastics could be used) and connected to the lead interface and component block 37 is the appropriate signal distribution network 36 commonly having and input/output bus and multiplexor sets of circuits. Switches from within a Control Logic block 35 provide a number (w) of signals to direct signal traffic through the multiplexers in circuit 36. If the discharge components are located on the lead conductor side of circuit 36, a pacing output block 25 is appropriate to this illustration. It will be recognized by one of ordinary skill in the art that the design and implementation features of the circuits included in block 36,37,25 and 35 will be appropriate to the specific device being designed. A sense amplifier system block 301, includes amplifier circuits which receive signals directly from the electrodes through circuits 37 and 36. Control logic 35 selects the availability of components in the sense amplifier system 301 to prevent amplifier saturation from overly large signals, control gain, and generally manage their function. An appropriate number of input lines (x) are provided to control this system. Details of this control are relevant to the emendation of the preferred embodiment of this invention as will be described later with reference to FIG. 3. Control logic 35 depends on timing circuit and crystal clock block 37 input lines (y) provided thereto as well as input from a CPU bus (not shown) providing signals from CPU block 26.

The CPU block 26 includes a microprocessor and associated input and output digital signal lines available either through control logic block 35 or directly to the various circuits within the implantable pulse generator 200. It may have micro coded instructions or be controlled by a program located in RAM/ROM block 27 to perform the various control functions and execute the various therapies employing the other circuits of the IPG 200.

Figure 2A:
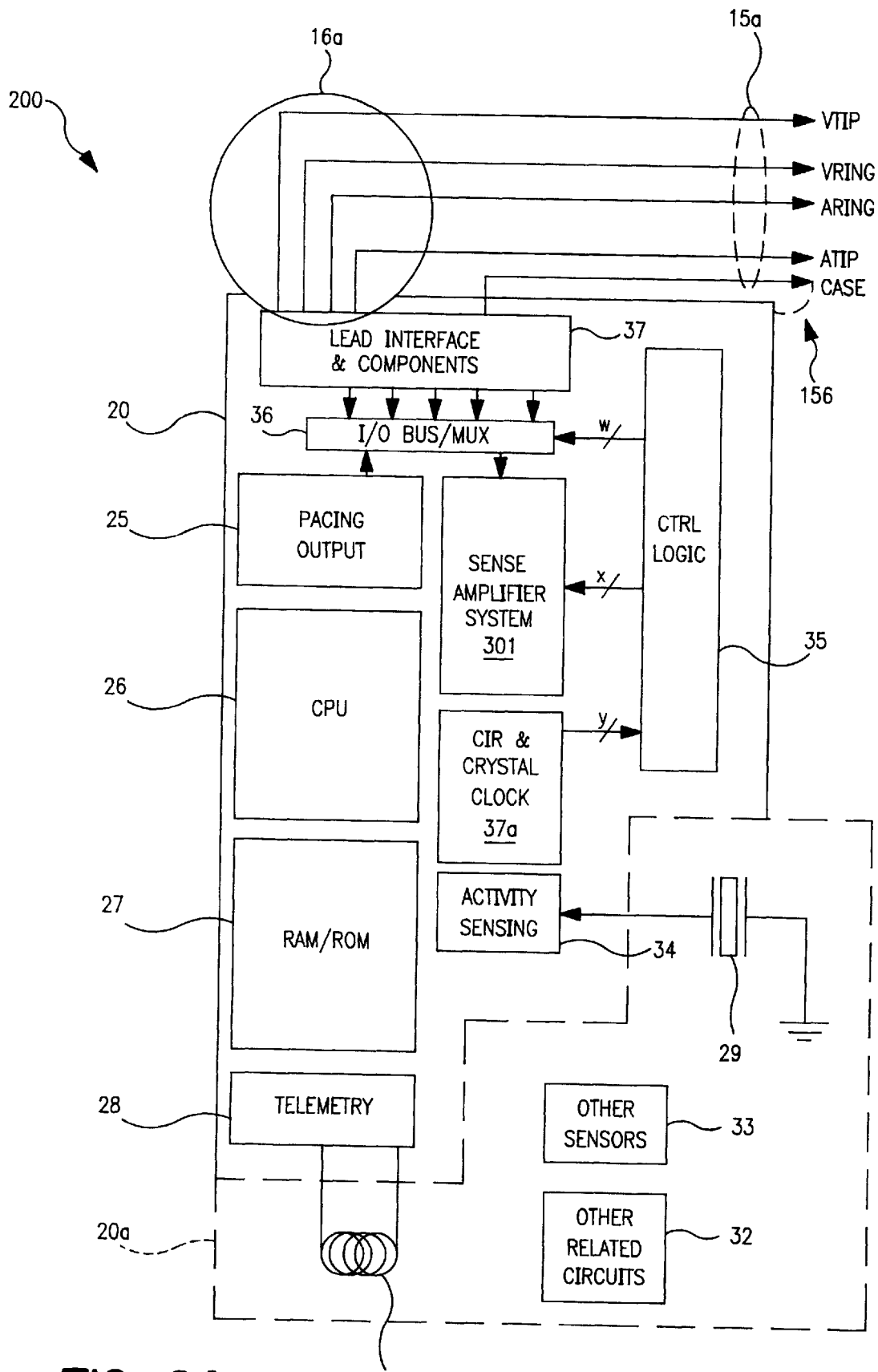
FIG. 2A is an alternative form of FIG. 2.

Additionally, a telemetry block 28 includes circuitry for sensing when communication is required and for providing both input and output data pulses in appropriate form for communication through antenna 31. The antenna 31 and activity crystal 29 as well as other sensors which maybe employed by the IPG 200 in block 33 may be located inside or outside of the hermetically sealed container of the IPG 200. This is indicated in the illustration by dotted line 20a in FIG. 2A. The activity sensing circuit 34 provides a function similar to the other sensor related circuits 32 which is to receive data from the sensors associated with that circuit and provide for output signals typically to the CPU bus or another data bus so that the measurement provided by the particular sensor maybe used by the IPG 200. Additionally, such circuits may turn on or turn off the function of a particular sensor associated therewith.

In FIG. 3 is a block diagram of the circuit system 300 most relevant to the inventive features of the present invention. To place the circuit in context with the implantable pulse generator, note that a data bus 30 communicates with the CPU RAM/ROM circuits and that lines 43 and 44 provide electrical connection to an atrial lead conductor AL and an ventricular conductor VL, respectively (the AL and VL conductor maybe either ring or tip depending on a previous switch setting not shown) The capacitors which provide the charge for the stimulating pulse are here illustrated as capacitor 41 and 42. (It should be noted that in a single conductor device, one set of these previously described features would not be required nor would multiplexer 40. Additionally a lot of the timing to be described with respect to this embodiment would also not be required.)

The data from the inventive circuit 300 is available to the micro processor on databus 30 for storage or high level processing by the lead integrity status registers in block 71 that provide signals 73 illustrated on the left side of the block 71. The signal present on these lines 73 is determined by input signals through status lines 74 from decode logic 72. Control registers in block 60 read out or read in signals in lead integrity status register 71 by providing read and write signals on bus 75. Timing that determine whether they should be read in or read out is provided by signals on lines 77 and 78 to an address decode register 70 which takes address information from lines 76 that may be used in a program presently executing in the CPU and RAM/ROM circuit elements described in respect to FIG. 2.

Timing and control circuit block 50 receives input from a clock signal circuit (not shown) and is enabled by information from the control register blocks 60 and 61b to provide timing signals to the other components of the diagram that are related to the part of the program being executed. For example, if the IPG is about to make an atrial unipolar pace, the timing and control circuitry will provide signals on line 51 to prepare circuits 48 to receive input signal at the appropriate moment, and to provide power for the remaining circuit blocks. Note that the threshold input CURAMP should have different inputs for the OCP and SCP threshold levels. Individual circuits which will be measuring the signal, will then set themselves with the appropriate thresholds for atrial unipolar pace, for this example, and an open circuit test.

With one of the capacitors 41 or 42 fully charged and beginning to discharge during a pace, the high impedance input of the voltage amplifier circuit 48 will have a direct electrical connection to that discharging capacitor across lines 45 and 45a, being directed there through multiplexer 40. A large resistor 46 is placed in the signal path 45b to the current amplifier circuit 49 to track the pacing voltage. This resistance value in the preferred embodiment is preferably 20 Mega ohms plus or minus about 5 percent, thus requiring an off chip resistor. Threshold and gain characteristics are thus provided across lines 61a to both circuits 48 and 49 simultaneously as indicated by the control registers in block 60. For example, an atrial unipolar pace pulse when testing for an open circuit (AOCP) would be typically looking for a value of greater than 4,000 ohms resistance ( versus 200 ohms for a short circuit pulse or "SCP"). Other values can be programmed in if desired. The duration characteristic of the pacing pulse being delivered is accounted for by the enable and disable signals being timed by circuit 50 to correspond to the pulse width. Typical values for a pacing pulse delivered by a pacemaker include a range of from less than 1 volt to over 7½ volts in amplitude and from 121 microseconds to 1.5 milliseconds pulse width. Line 61 threshold information provides to circuits 48 and 49. The gain is provided along line 61a. At as close as possible to the moment of the closing of the pacing switch which provides the pacing pulse current across the lead conductor, signals on line 51 signal the appropriate circuits to turn on and measure what is at their input. This signal could be as simple as a set of clock signals or as complicated as is desired by the designer.

Figure 4:
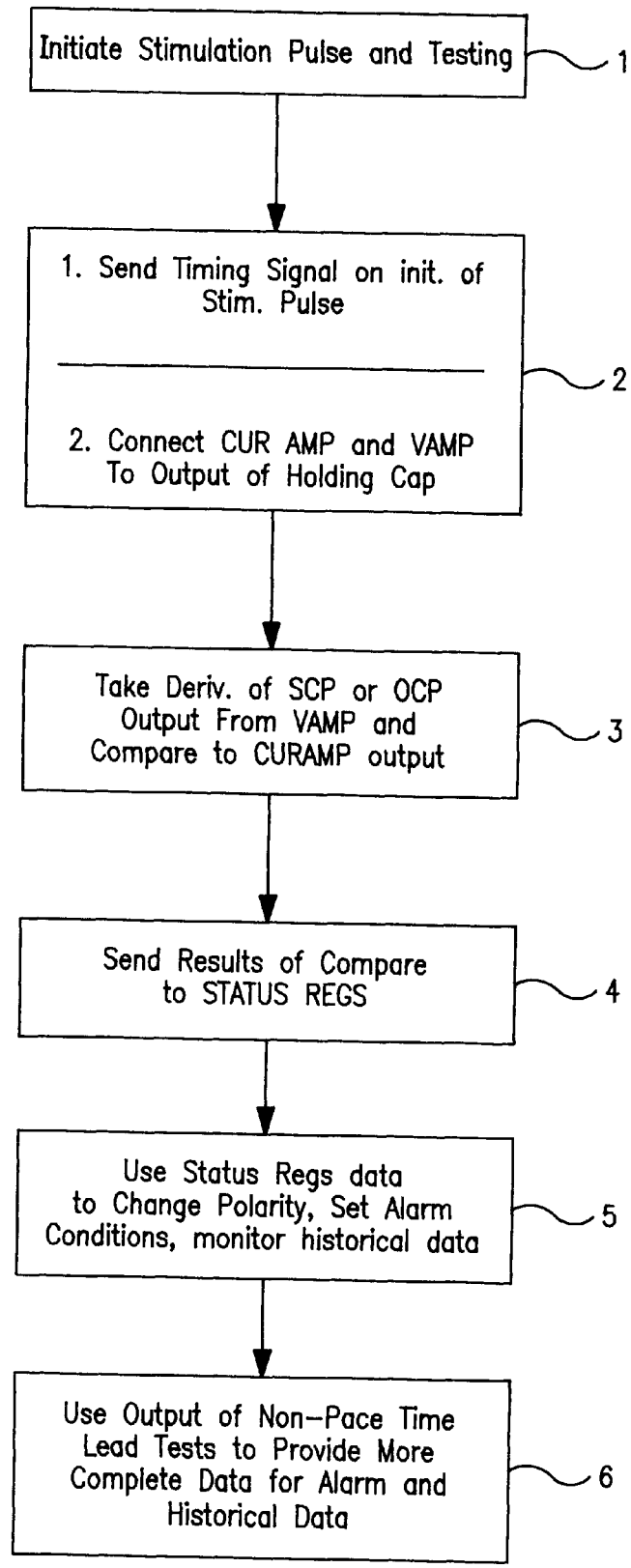
FIG. 4 is a flow diagram for use of the generalized form of this invention.

The basic operation of circuit 300 is designed to monitor the current delivered to the heart (in the pacemaker embodiment) during each pace and to flag excessively high or low current levels as indictors of leads status. In a generalized form this activity is illustrated by the flow diagram of FIG. 4, steps 1–6. The pacing voltage is also monitored such that if current increases as pacing voltage is increased for the same pacing load, such a condition does not set the lead status indictor flags. Circuit 300 measures the voltage on the external 10 uF stimulating pulse holding capacitors via the current through the 20 Mega ohm hybrid resistor. The pacing current is determined through an equation, Ip=Ch*(d Vch/dt), where Ip is the pacing current, Ch is either the atrial or the ventricular pace holding capacitor value, and Vch is the voltage across the holding capacitor. The pacing current is compared to threshold currents to determine if the pacing impedance exceeds a high impedance threshold and is below a low impedance threshold. High impedance paces are called open circuit paces (OCPs) and low impedance paces are called short circuit paces (SCPs).

The function of circuit 48 can be described as a AC coupled amplifier. Its outputs 91 and 92 feed into derivative (dv/dt) detector circuits 81 and 82 that generate output current proportional to the slope of their input voltage. The current amplifier 49 receives input current proportional to the voltage on the holding capacitor received through line 45, that is selected by the input multiplexer 40. Circuit 49 functions as a current amplifier. The gains of both circuits 48 and 49 are programmable to provide various OCP and SCP thresholds and may be adjusted by input from line 61a. This of course, is related to whether circuit 300 is currently testing for a ventricular or an atrial pace. Because the timing circuit directs the turning on and off of these circuits, pulse width changes are not a concern. Because the "on" time is roughly equivalent to the width of a pacing pulse, the opportunity for double pacing is presented by this circuit. Double pacing is discussed below.

As will be apparent to the reader of ordinary skill in this art, all of the signals provided on lines 88a, 88b, 87a, 87b and 88 and 87 maybe in either a digital or analog form and still provide the same result. This will become more apparent with a description of the circuit blocks 81 through 86 as follows.

We will start with an open circuit pace detection. The programmable gain for circuit block 48 for the OCP detect channel will be higher than the gain for an SCP channel in general. By programming the gain of circuit 48, to keep its output within a range acceptable to the derivative detector circuit 82, circuit 82 is not subjected to a wide range of input slew's for various OCP thresholds. The output value provided by detector 82 is compared to the output of current amp circuit 49, if an analog output than the comparison occurs because of a connection at 88, otherwise both would be provided to the current comparator 84 as digital signals of some numeric value representing the measurement results.

The pace follows OCP or SCP conditions with bipolar pacing lead and is in the nature of a backup unipolar pace. Preferably, for the SCP condition the device will be provided with a third or additional pacing capacitor 501, the charge of which can be directed by a circuit like 500 to the SCP lead (Pacing Lead) continuing to the pace on discovery of the SCP condition in a bipolar configuration as in FIG. 5.

It should be noted that since for the same pacing load, circuits 82 and 49 output current proportional to the same pace amplitude, the dependence of thresholds to paced amplitude is eliminated.

Figure 5:
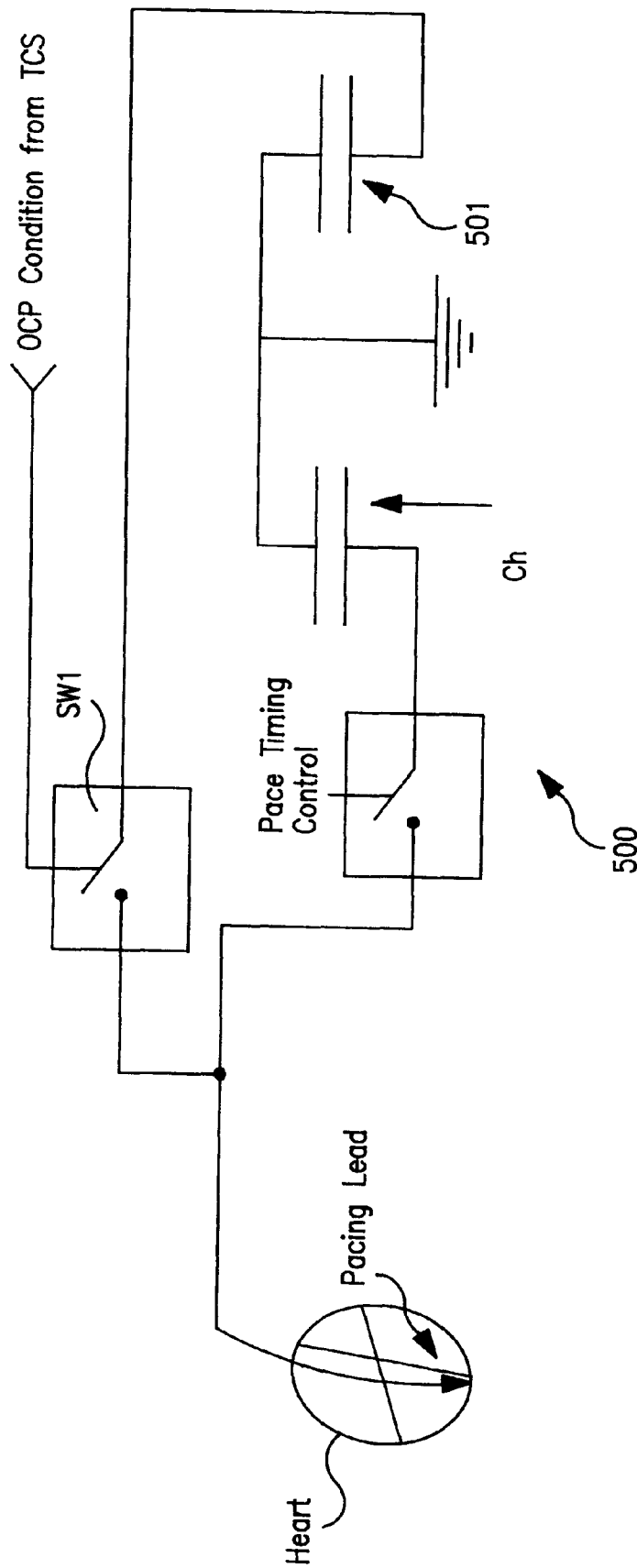
FIG. 5 is a circuit diagram for use with an extra circuit element for holding additional charge for a double pace, preferably used after a short circuit is detected.

In the analog form, the output of circuit 84 will remain low (or high depending on the designers indicator of choice) as an indication of an open circuit pace if the output of detector 82 is less than the output current of the current amplifier circuit 49. This output maybe either indicative of an OCP condition in an atrial bipolar, a ventricular bipolar, an atrial unipolar, or a ventricular unipolar pace, depending on the signal supplied on line 51 to decode logic 72 and open circuit logic 86. Since these circuits determine a short or open circuit condition during the pulse delivery an opportunity is provided to deliver a second pace immediately. This we call a "double pace". By providing a signal across line 302 from the decode logic 72, as soon as any positive indication of a bipolar OCP or SCP condition is found, the timing circuit 50 (or other circuit designed for this purpose if preferred) can generate a signal to enable the discharge of a double pace in a unipolar configuration, essentially by either turning on the extra capacitor or charge circuit as is illustrated in FIG. 5 or by using residual charge on the capacitor just previously made available to provide a stimulation pulse to tissue, in the case of an open circuit, since in the OCP case there will be sufficient charge remaining. At the same time the timing circuit should extend the time the measurements are being made by the CURCOMP and VAMP circuits and those down stream from them.

When the voltage circuit 48 is programmed to provide output through the SCP output line 91 to detector circuit 81 the gain is adjusted appropriate to a short circuit test (and a much lower impedance) and the threshold is programmed accordingly. The amplified signal drives circuit 81 and, as in the case with the OCP detector 82, the output with circuit 81 is compared with the output of current amp circuit 49 using current comparator circuit 83. This current comparator circuit 83 will output a logic high(or opposite to whatever logic is provided by output circuit 84) if the SCP threshold current is exceeded at anytime during the pacing pulse being measured.

Figure 6:
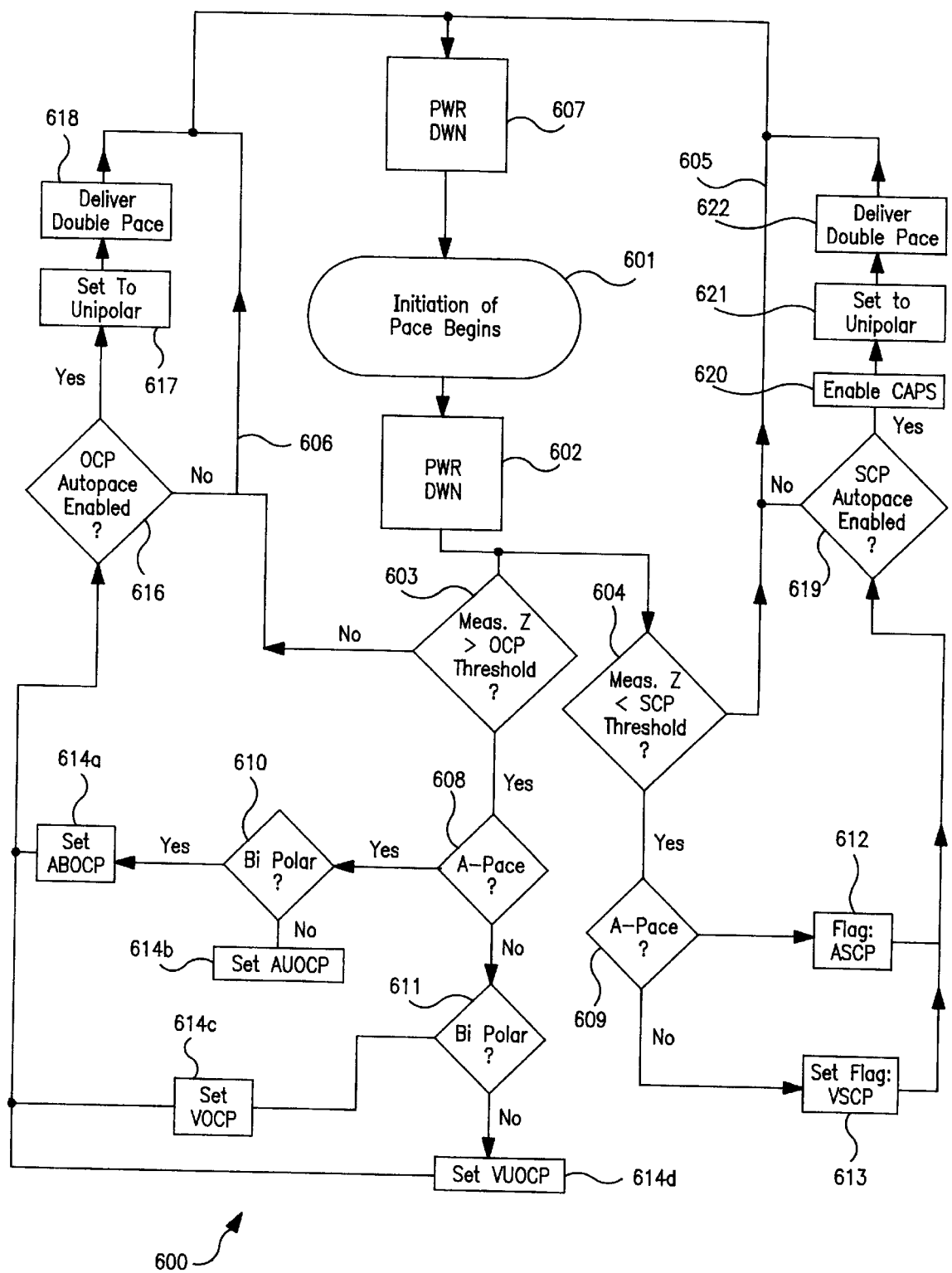
FIG. 6 is a flow diagram detailing the operation of a preferred embodiment lead pacing stimulation impedance measurement device in accord with a preferred embodiment.

FIG. 6 is a block flow diagram 600 illustrating the order in which the events within these circuits take place. This process initiates when a pace begins (601) and the first step 602 is to power up the circuitry. The circuits then measure the impedance and determine whether it is over the OCP threshold 603 and or less than the SCP threshold 604. If it is outside either threshold the circuit may again power down to 607 and await the initiation of a new pace at step 601. This measure of impedance is the output of lines 93,94, and 96 from FIG. 3's circuit 300.

A decision must be made concerning whether this was an A Pace or V Pace(that is, and Atrial Pace event or a Ventricular one) and this decision is made in steps represented here by blocks 608 and 609 of flow chart 600 by the decode logic 72 of circuit 300. If there is a short circuit pace condition it doesn't matter whether it's a Unipolar or a Bipolar short circuit the same atrial short circuit pulse (ASCP) flag will get set in step 612, or ventricular short circuit pace (VSCP) flag 13 will get set in the next step 613. If in step 619 it is determined that a short circuit pulse autopace is enabled, line 302 will be available in circuit 300 to provide information to the timing control circuit 50 that there has been a short circuit pace. If this is the case, the extra capacitor (capacitor 501 of circuit 500) will be enabled in step 620, if there is such a reservoir of charge available in the device being controlled by the circuit operating in accord with this flow chart. If not set already to Unipolar configuration as determined in step 619a step 621 will do so before the double pace pulse is delivered in step 622. After the double pace has passed a signal will start the power down operation in step 607 which would otherwise have been initiated by the outputs of also available in line 605.

If a determination has been made that an impedance level is greater than the OCP threshold in step 603, and the determination that this is an atrial pace has been made in steps 608, a determination in 610 is made as to whether to set the flag ABOCP in step 614a or AUOCP in step 614b to identify on the data bus 30 the lead integrity status for the particular configuration(that is, Atrial Unipolar or Atrial Bipolar).

If it is not an atrial pace, we know it must be a ventricular pace and in step 611 the circuits again determine whether or not it's bipolar. If its not, flag VUOCP is set in step 614 or VBOCP is set in step 614c if it was bipolar. Whatever flag is set the next step 616 makes a determination as to whether or not the OCP has an autopace enabled feature and if so assures that the next pulse will be delivered in a Unipolar configuration in step 616, to be delivered in step 618. After delivery of the double pace pulse in step 618 circuit 300 will be powered down in step 607 if it has not already been powered down by the other inputs on line 606. Note also that if the OCP in Uni-polar mode, the preferred systemic response would be to not deliver a double pace in unipolar mode since, unipolar pacing is shown to be ineffective. Thus in the preferred system a step 616a simply provides for a power down step (607) in the case of an OCP in unipolar mode.

Additionally, these circuits and other features described above can be used together with the impedance measurements made by other systems, preferably those which check for lead integrity at times other than during the pacing pulse. The most preferred system would be that described in the patent application by this inventor on even date with the filing of this application entitled Non-Physiologic Sense Detection, Ser. No. 08/966,107 hereby incorporated herein in its entirety by this reference.

By using an alternative measurement with this one, more data can be collected regarding the time of occurrence of a lead circuit integrity issue. The data will also cover more mechanical heart positions than a device which measures only either during the delivery of a pulse or when one is not being delivered and the sense amplifier blanking is not on. Such not-during-a-pace data could be supplied by any of the methods and device teachings described by the patents in the background section except those which measure at some part of the pacing pulse delivery time. Data generated by any of these measurements can easily be compiled and stored in a suitable format in memory within the IPG. This data in memory could be used to provide the basis for a program that generates a patient alarm, or can be read out by communications between the IPG and an external device whereby a clinician can use the data for whatever purpose, including scheduling replacement of a bad lead, changing pacing parameters and so forth, as well as for reporting to the manufacturer. If the occurrence of a bad lead in bipolar condition is established, the IPG can automatically switch on a sustained basis, to unipolar mode.

Though the invention has been described in detail, many variants on it will occur to those of ordinary skill in this art. Therefore, it is only to be considered limited by the following claims.

What is claimed is:

1. A medical electrical lead measurement circuit for use inside a hermetically sealed housing of an implantable pulse generator(IPG), said IPG having a connector member for electrically connecting a medical electrical lead conductor to a discharge circuit element, said element for providing current through said lead conductor to tissue in a body with which said lead is designed to be electrically connected by an electrode to be associated with said tissue, and also having means for connecting said lead conductor and said discharge means to said medical electrical lead measurement circuit said circuit further comprising:

Voltage amplifier (VA) means for amplifying a voltage variation found on said lead conductor during a stimulating pulse delivered through said lead conductor from said discharge circuit element, Derivative Detector circuit means for receiving an output from said VA amplifier and generating at a Derivative Detector's output a current proportional to a slope in the variation found on said VA amplifier output over a time determined by and substantially commensurate with the length of said pacing pulse, Current Amplifier circuit connected to said discharge means across a resistor circuit member for generating a current proportional to the voltage on said discharge means during said stimulating pulse, and circuit comparator means for producing a signal indicating a condition of said lead conductor based on a comparison of the outputs of said Derivative Detector and said Current Amplifier.

2. A medical electrical lead circuit as set forth in claim 1, further comprising: Signal indicator means for producing a signal indicating whether said lead condition represents an open circuit, a short circuit or a normal circuit based upon an output from said circuit comparator means.

3. An implantable pulse generator having a circuit as set forth in either of claims 1 or 2.

4. An IPG for use with a medical electrical lead circuit as set forth in claim 1, further comprising: an additional charge holding source for providing current which may be needed to deliver a double pace on the occurrence of a condition of a bipolar short circuit pace.

5. An IPG for use with a medical electrical lead circuit as set forth in claim 4 wherein said additional source may also provide current to deliver a double pace on the occurrence of a bipolar open circuit pace.

6. An IPG for use with a circuit as set forth in claim 1, having additional switching circuit means to switch between an atrial charge source and a ventricular charge source in said IPG such that for an atrial pace said atrial source is switched to be connected to said measuring circuit while during a ventricular pace said ventricular charge source is switched to be connected to said measuring circuit.

7. An IPG having a circuit as set forth in claim 1, further having polarity switching circuit means to switch from a bipolar pacing configuration to a unipolar pacing configuration responsive to an occurrence of an indication from said measuring circuit of an open or short circuit in the medical electrical lead conductor under test.

8. An IPG as set forth in claim 7, having assurance of unipolarity circuit means to assure that said IPG is in unipolar configuration for the delivery of a double pace.

9. A method for measuring impedance during the duration of a stimulating pulse wherein said pulse is for delivery to bodily tissue comprising:

providing predetermined threshold information regarding the level of measurement to be interpreted by a current amplifier and by a voltage amplifier as open and short circuit stimulating pulses, upon the initiation of delivery of a stimulating pulse, measuring the current at said current amplifier at a connection of a charge delivery device, said charge delivery device providing the charge for said stimulation pulse, through a relatively large resistor, while simultaneously measuring the voltage from said charge delivery device at a high input impedance connection of said charge delivery device to said voltage amplifier, providing output signal values for open circuit pace and closed circuit pace measurements made by said current and voltage amplifiers, taking the derivative of the short circuit and open circuit values from said voltage amplifier and producing a signal value representative thereof, comparing the open circuit value derivative value to the open circuit value produced by the current amplifier and comparing the short circuit derivative value and the short circuit value from the current amplifier, based on said comparisons, determining whether there is an open circuit, a short circuit or a normally functioning circuit condition on a lead connected to said charge supply element.

10. A method as set forth in claim 9, and further comprising the step: producing an indicator value representative of whether there is an open short or normal circuit.

11. A method as set forth in claim 10, further comprising the step: storing values representing said indicator value.

12. A method as set forth in claim 10, further comprising double pacing if said indicator value shows an open circuit or short circuit condition.

13. A method as set forth in claim 10, further comprising the steps of:

measuring impedance of a lead during non stimulation time periods and deriving a signal from said measurements indicating whether an open or short circuit is apparent, and evaluating the occurrence of indicators from claim 10 together with said non stimulation time period indicator to determine if a bad lead condition exists and responding to said bad lead condition.

14. A method as set forth in claim 13, wherein said responding step includes setting an alarm.

15. A method as set forth in claim 13, further comprising: recording the indication for later transmission to an external device.

16. A method as set forth in claim 13 further comprising the step of;

recording said indicators.

17. A method as set forth in any of claims 10–14, or 16, and further comprising the step of permanently changing pace polarity to unipolar with a bipolar lead.

18. A method as set forth in any of claims 10 –14 or 16, comprising the further step of telemetering out said indicators to an external device.

19. A method as set forth in claim 9, further comprising: changing the polarity of pacing from bipolar to unipolar if a short or open condition is found during a bipolar pace.

20. A method as set forth in any of claims 9–19, further comprising:

measuring impedance of a lead during non stimulation time periods and deriving a signal from said measurements indicating whether an open or short circuit is apparent, and recording said non stimulation time period indicator.

* * * * *